United States Patent [19]

Morrison

[11] 4,423,630
[45] Jan. 3, 1984

[54] CYCLIC POWER MONITOR

[76] Inventor: Thomas R. Morrison, 137 Overlook St., Mount Vernon, N.Y. 10552

[21] Appl. No.: 275,334

[22] Filed: Jun. 19, 1981

[51] Int. Cl.³ .............................................. G01L 5/02
[52] U.S. Cl. ............................... 73/379; 272/DIG. 5; 340/323 R
[58] Field of Search ................ 73/379, 862.19, 862.27, 73/862.28; 128/774, 779; 272/DIG. 5, DIG. 6; 340/323, 573; 364/413, 415

[56] References Cited

U.S. PATENT DOCUMENTS

| | | | |
|---|---|---|---|
| 667,920 | 2/1901 | Perkins | 73/862.27 |
| 3,643,943 | 2/1972 | Erwin, Jr. et al. | 272/DIG. 5 |
| 3,744,480 | 7/1973 | Gause et al. | 73/379 |
| 3,797,010 | 3/1974 | Adler et al. | 272/DIG. 5 |
| 4,099,713 | 7/1978 | Spector | 73/379 X |
| 4,141,248 | 2/1979 | Bargenda | 73/379 |
| 4,199,987 | 4/1980 | Bauers et al. | 73/379 |

*Primary Examiner*—Charles A. Ruehl
*Attorney, Agent, or Firm*—Thomas R. Morrison

[57] ABSTRACT

A cyclic power monitor measures a cyclically applied force applied by animal muscle power to a device and calculates the work done by the application of the force. The time between cyclic applications of the force is calculated to produce a value which may be used to divide the calculated work to calculate applied power. An indicating device may be employed to indicate departure in applied power from a predetermined value. A cadence alarm may be employed by itself or in combination with the cyclic power monitor to indicate departures in cadence of the pedalling effort from a predetermined value of cadence. In addition, departures in the force applied to the device from a predetermined force may also produce an indication for the operator.

7 Claims, 3 Drawing Figures

CYCLIC POWER MONITOR

BACKGROUND OF THE INVENTION

The present invention relates to power monitors and, more specifically, to power monitors adapted for monitoring a cyclic, or periodically applied, power output of muscular origin.

In athletic endeavors, it is well known that the endurance of an athlete is related to the rate at which the athlete expends energy. A sprint by a bicycle racer, for example, produces a high velocity over a short distance but reduces the athlete's longterm ability to cover a long distance at the highest overall speed.

A trained bycycle rider may be capable of producing as much as 0.75 horsepower for short bursts but, for a longer period, a power of 0.15 horsepower applied to the pedals of a bicycle represents the maximum effort sustainable for an hour or two. For a lesser athlete, a sustainable output power may be substantially less than this.

In bicycle racing, or even bicycle touring, with a bicycle having a number of different gear ratios and operating in an environment having wind, hills and riding surfaces of varying resistance to a wheel, it is difficult to maintain a combination of pedal force and gearing which will produce a desired maximum speed over a time long enough to cover the required distance.

OBJECTS AND SUMMARY OF THE INVENTION

Accordingly it is an object of the invention to provide a cyclic power monitor for monitoring a cyclic muscular output power.

It is a further object of the invention to provide a cyclic power monitor which measures a cyclic muscular output power, compares the measured output power with a predetermined output power and actuates an indicating device in response to the comparison.

According to an aspect of the invention, there is provided a method of monitoring a muscular source of cyclic power, wherein the cyclic power is periodically produced by a periodically applied force acting through a distance, comprising measuring application of the force, comparing at least one characteristic of the force with a predetermined value of the at least one characteristic, and indicating at least one result of the comparison.

According to a feature of the invention, there is provided a method of monitoring a muscular source of cyclic power, wherein the cyclic power is periodically produced by a periodically applied force acting through a distance, comprising measuring the force, multiplying the force times the distance to produce a work signal, calculating a cyclic time interval of the periodically applied force, dividing the work signal by the cyclic time interval to produce a power signal, and indicating the power signal.

According to a further feature of the invention, there is provided a method of monitoring a muscular source of cyclic power, wherein the cyclic power is periodically produced by a periodically applied force acting through a distance, comprising calculating a cyclic timer interval of the periodically applied force, and indicating the cyclic time interval.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

The present invention can be applied to measure the muscular power output derived from any cyclically applied force applied through a distance. For example, the power output of oarsmen in a rowing competition and other such cyclic athletic activities may be monitored. For concreteness of description, however, a cyclic power monitor for bicycle pedalling is described in detail.

As is well known, where a force F is applied through a distance s, the resulting work W performed is:

$$W = Fs$$

Also, power P is equal to:

$$P = dW/dT$$

Where T = time.

Figure 1:
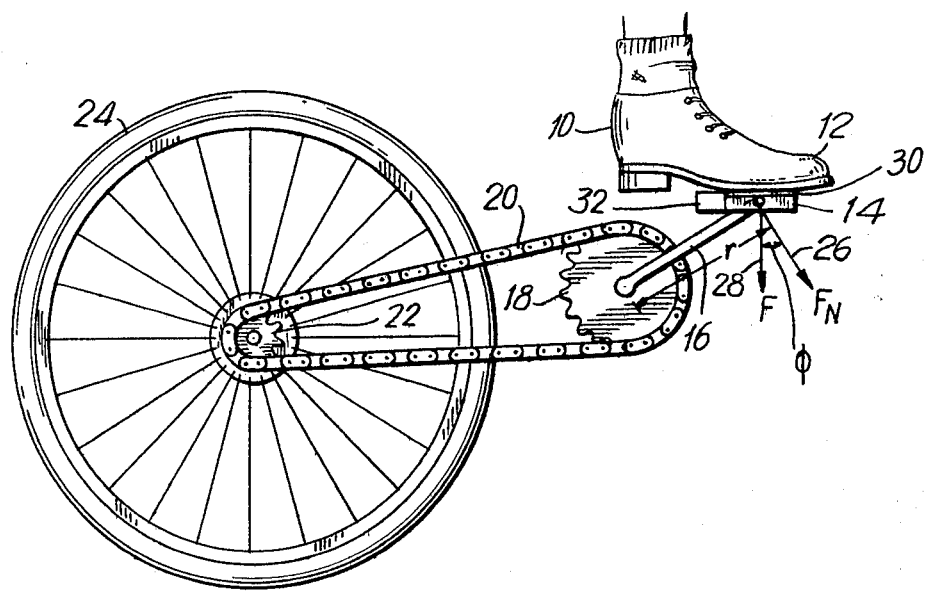
FIG. 1 is a partial view of a bicycle on which an embodiment of the invention may be employed.

Referring now to FIG. 1, a foot 10 of a bicyclist is shown with its toe 12 resting on a pedal 14. Pedal 14 is connected by a crank arm 16 having a length r to a conventional sprocket 18. Sprocket 18 is connected by conventional means such as, for example, a roller chain 20 to a rear sprocket 22 which is conventionally coaxially coupled to a rear or driving wheel 24.

A conventional gear-changing apparatus, either internal to a hub of wheel 24, or on sprocket 18 and rear sprocket 22, may be used to change the ratio of turns of sprocket 18 to turns of driving wheel 24. That is, by suitably changing the gear ratio for a given speed of wheel 24, sprocket 18 may be required to turn faster or slower. However, as the gear ratio is changed to increase or decrease the speed of sprocket 18, the normal force $F_N$ which must be applied to pedal 14 along a line 26 normal to the axis of crank arm 16 in order to maintain a given torque on driving wheel 24 is changed in the opposite sense. That is, if the gear ratio is changed so that the speed of sprocket 18 must double for a given speed of driving wheel 24, normal force $F_N$ to maintain the same torque on driving wheel 24 is reduced to one half of its previous value.

It will, of course, be recognized that the muscular power output applied by toe 12 is not measured along the direction of the normal force $F_N$. Instead, the bicyclist's power output is measured in the direction of applied force F along a line 28 which is displaced from line 26 of normal force 26 by an angle $\phi$. Angle $\phi$ varies throughout the effective half rotation of crank arm 16 during which toe 12 is descending.

A load cell 30 is interposed between toe 12 and pedal 14. Load cell 30 may be of any type effective to change an electrical characteristic thereof in response to the applied force F. A piezoelectric material which produces a voltage in response to applied force F, a strain gauge which changes its resistance in response to applied force F or any other suitable technique may be used. In the preferred embodiment, load cell 30 includes a body of conductive rubber of the type which exhibits a change in resistance in response to applied force F.

An electronics package 32 may conveniently be affixed to pedal 14 by any convenient means to receive signals from load cell 30, to perform the required calculations, and to produce the desired indications.

Figure 2:
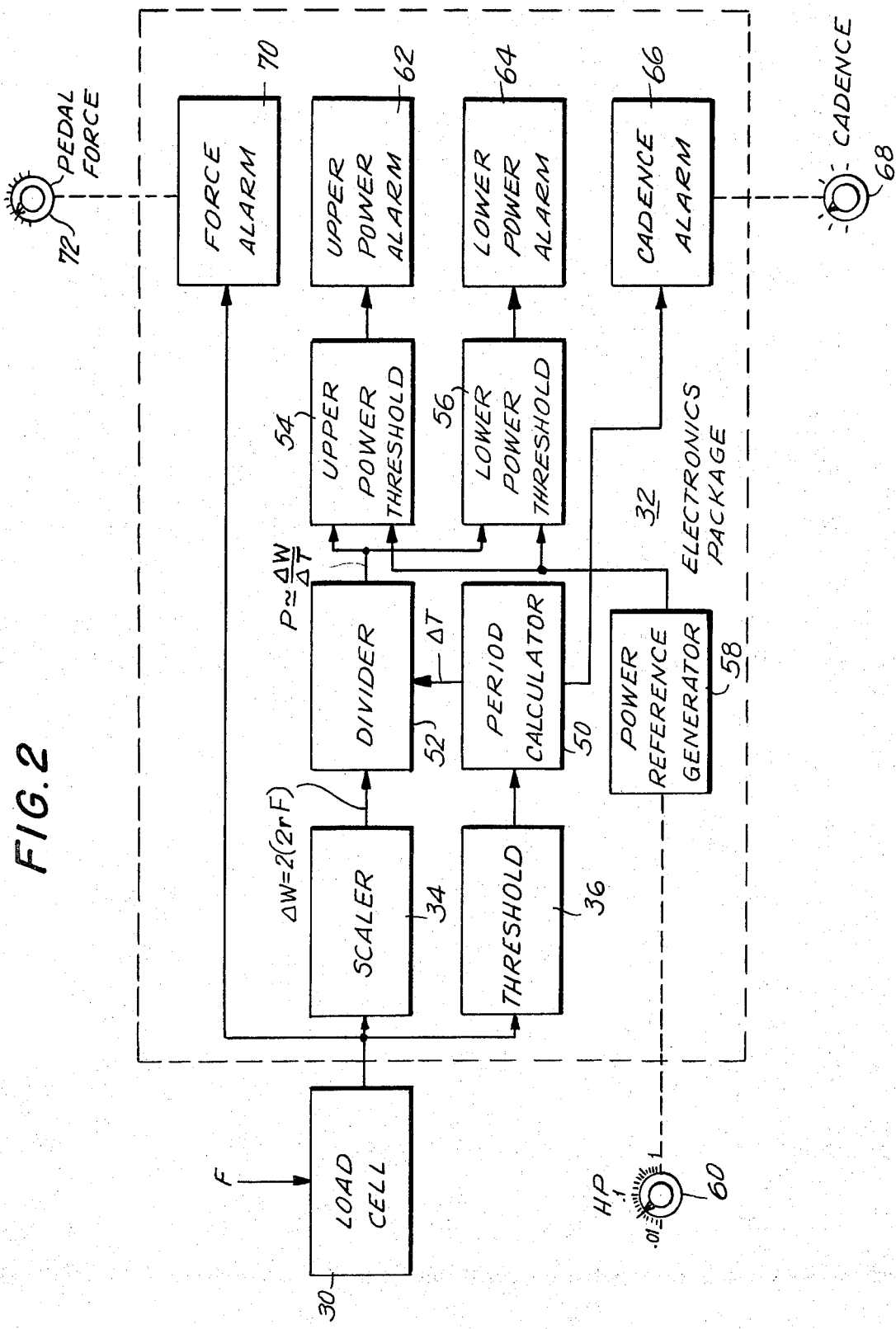
FIG. 2 is a block diagram of a cyclic power monitor according to an embodiment of the invention.

Referring now to FIG. 2, load cell 30 receives mechanical input F and applies a signal proportional thereto to a scaler 34 and to a threshold 36. Scaler 34 multiplies force F by a constant 2r since this is the distance travelled by toe 12 (FIG. 1) in the direction 28 during the downward motion. An additional factor of 2 is applied by scaler 34 since, in the embodiment shown in FIGS. 1 and 2, only the power applied by one foot is calculated. Since two feet are employed to power a bicycle, the additional factor of 2 accounts for this. The output of scaler 34 is an increment of work $\Delta W$ produced during the full pedal cycle during which force F is applied to each of two pedals.

The above assumes that force F is constant during downward travel and that both of the cyclist's feet apply substantially the same force. For most practical purposes, these assumptions are close enough since the object of the invention is not so much precision in measurement of the power output as comparison of power output relative to an arbitrarily defined standard as will be described.

Figure 3:
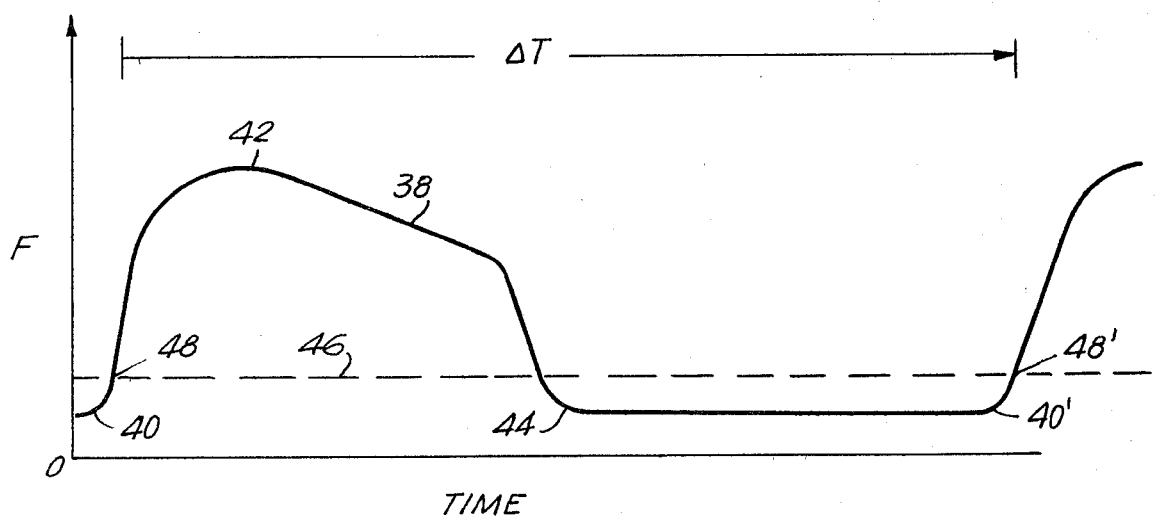
FIG. 3 is a graph of applied force versus time to which reference will be made in describing the embodiment of the invention in FIGS. 1 and 2.

Referring now to FIG. 3, a curve 38 is shown representing force F with respect to time. Just after pedal 14 passes the top of its travel, force F begins to rise at a point 40 as the cyclist presses on pedal 14. Force F rises to a peak at a point 42 and then decreases to a minimum value at a point 44 as pedal 14 passes the bottom of its travel and the foot on the opposite pedal is depended upon to provide power from point 44 until a point 40' at which time the pedal 14 being monitored again receives substantial power.

It should be noted that force F does not fall to zero in the inactive period from point 44 to point 40' since pedal 14 must support and raise the weight of foot 10, including the weight of the cyclist's leg during this time.

In order to establish a measurable event from which the cyclic time interval $\Delta T$ of a pedal crank revolution can be determined, threshold circuit 36 produces an output signal each time force F exceeds a predetermined value in the positive-going direction. In FIG. 3, a dashed line 46 higher than minimum value at points 40, 44 and 40' represents a threshold value of force F. At points 48 and 48', force F exceeds threshold 46. The time between points 48 and 48' is approximately equal to a period $\Delta T$ of a pedal revolution. A period calculator 50 (FIG. 2) receives the positive-going threshold-crossing signals from threshold 36 and produces a signal $\Delta T$ proportion to the time between a predetermined number of these events.

The increment of work $\Delta W$ from scaler 34 and the cyclic time interval signal $\Delta T$ from period calculator 50 are applied to a divider 52 which calculates an approximation of the power $P \simeq W/T$.

Power signal P is applied to an upper power threshold 54 and to a lower power threshold 56. A power reference generator 58 produces a power reference signal in response to a manually controllable input signal from, for example, a control knob 60 which is calculated in units of power such as, for example, foot-pounds per second, watts or horsepower. The power reference signal from power reference generator 58 is applied to upper power threshold 54 and lower power threshold 56.

When the power signal P exceeds an upper threshold established in upper power threshold 54 by the threshold signal applied thereto due to excessively rapid pedalling and high applied force F, upper power threshold 54 produces a signal which energizes an upper power alarm 62 which informs the cyclist that he should select a higher gear or reduce force F. The output of upper power alarm 62 may be audible, such as a tone, visible, such as a light or a combination of these. For example, upper power alarm may produce a series of constant-frequency tones spaced about 0.5 seconds apart which the cyclist can interpret as advice to select a higher gear.

Similarly, when power signal P is less than a lower threshold established in lower power threshold 56 by the threshold signal applied thereto due to excessively slow pedalling and low applied force F, lower power threshold 56 produces a signal which energizes a lower power alarm 64 which informs the cyclist that he should select a lower gear or increase force F.

In cycle touring and cross-country racing, there is an optimum cadence or cyclic time interval $\Delta T$ for each cyclist which contributes to the endurance of the cyclist. A cadence alarm 66 compares the measured cyclic time interval $\Delta T$ with a desired cadence which may be manually set by a cadence control 68 and, if the measured quantity departs from the manually set quantity by more than a predetermined value, an alarm indicative of this fact may be produced. As in the case of power, cadence alarm 66 may produce a high alarm and a low alarm indicative of excessive or insufficient pedal speed. The cyclist may thereupon change gears in the appropriate direction in response to the cadence alarm to bring the measured cyclic time interval $\Delta T$ within the predetermined value of the selected cadence.

It would be clear to one skilled in the art that the measurement and indication of departures of cyclic time interval $\Delta T$ from a predetermined cadence is a useful function in its own right independently of the measurement and thresholding of power. Thus the power indication and cadence indication may each be considered as separate embodiments of the invention equally with an apparatus which includes both functions.

Cadence alarm 66 may also have a power-off function. That is, when no signal is received from period calculator 50 for a predetermined period, say 5 seconds, cadence alarm 66 may be employed to shut off unneccessary circuits to conserve power.

Although cadence alarm 66 receives its inputs from load cell 30 processed by threshold 36 and period calculator 50, other means for determining cyclic time interval $\Delta T$ may be employed. For example, an arm (not shown) may extend from electronics package 32 and may contact crank arm 16 once per revolution of sprocket 18. Alternatively, electronics package 32 may be mounted on a stationary portion of the bicycle and a contact arm may be contacted by crank arm 16 once per revolution to produce the timing signal for the determination of cyclic time interval $\Delta T$.

A force alarm 70 may be provided responsive to the output of load cell 30 and a selectable pedal force selected by a manual pedal force control 72 to indicate departure of the measured force from the selected force. Force alarm 70 may be employed in conjunction with upper and lower power alarms 62 and 64 and/or with cadence alarm 66 to aid the cyclist in his control of the bicycle.

It would be clear to one skilled in the art that each of the measured quantities specified in the foregoing may be employed to drive a meter which the cyclist may read rather than to actuate an audible or visual alarm. Such a method of indication should be considered to be within the spirit and scope of the invention.

Having described specific embodiments of the invention with respect to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Apparatus for measuring athletic performance of a bicycle rider comprising:
   means for sensing a force on a pedal of a bicycle effective to produce a force signal related to a force applied to said pedal by said bicycle rider;
   means responsive to said force signal for detecting a predetermined event in each rotation of a pedal crank of said bicycle and for producing an output signal in response;
   means responsive to said output signal for calculating a period between said events; and
   means responsive at least to said period for calculating at least one parameter of said athletic performance.

2. Apparatus according to claim 1 wherein said means responsive at least to said period includes means for calculating a cadence.

3. Apparatus according to claim 2 wherein said means responsive at least to said period includes means responsive to said force signal and said cadence for calculating a power output of said bicycle rider.

4. Apparatus according to claim 2 wherein said means for calculating a cadence includes means for indicating said cadence.

5. Apparatus according to claim 1 wherein said means responsive at least to said period includes means responsive to said force signal and said period for calculating a power output of said bicycle rider.

6. Apparatus according to claim 5 wherein said means for calculating a power output includes means for comparing said power output with at least one threshold value of power output and for producing an indication in dependence on a result of said comparing.

7. Apparatus according to claim 1 wherein said apparatus comprises a unitary package attachable to said pedal.

* * * * *